United States Patent [19]

Hirsch

[11] 4,097,240

[45] Jun. 27, 1978

[54] PROCESS FOR THE PRODUCTION OF A DIAGNOSTIC AGENT FOR THE DETECTION OF KETONES

[75] Inventor: Wolfgang Hirsch, Wunstorf, Germany

[73] Assignee: Riedel-de Haen Aktiengesellschaft, Seelze, Hanover, Germany

[21] Appl. No.: 767,028

[22] Filed: Feb. 9, 1977

[30] Foreign Application Priority Data

Feb. 11, 1976 Germany .............................. 2605221

[51] Int. Cl.$^2$ ............................................. G01N 33/16
[52] U.S. Cl. ............................. 23/253 TP; 23/230 B; 252/408
[58] Field of Search ....................... 23/230 B, 253 TP; 252/408

[56] References Cited

U.S. PATENT DOCUMENTS

| 2,990,253 | 6/1961 | Smeby | 23/253 TP |
| 3,212,855 | 10/1965 | Mast et al. | 23/253 TP |

FOREIGN PATENT DOCUMENTS 1,369,138   10/1974   United Kingdom ............ 23/253 TP

*Primary Examiner*—R.E. Serwin
*Attorney, Agent, or Firm*—Curtis, Morris & Safford

[57] ABSTRACT

In the process for the production of a diagnostic agent for the detection of ketones, consisting of an absorbent carrier impregnated in a first stage with an aqueous solution of an amino acid and tetrasodium ethylenediamine tetraacetate as buffer, dried and impregnated in a second stage with a solution of sodium nitroferricyanide in a solvent mixture one component of which is methanol and dried again, the improvement which comprises using as the second component of the solvent mixture, instead of dimethyl formamide, which is considered detrimental to health, quite a number of other solvents.

6 Claims, No Drawings

PROCESS FOR THE PRODUCTION OF A DIAGNOSTIC AGENT FOR THE DETECTION OF KETONES

The present invention relates to a process for the production of a diagnostic agent for the detection of ketones consisting of an absorbent carrier impregnated with sodium nitroferricyanide, an alkaline buffer and a water soluble lower amino acid, which comprises first impregnating the absorbent carrier with the amino acid and an aqueous solution of the tetrasodium salt of ethylenediamino-tetraacetic acid as buffer, drying the impregnated carrier, impregnating the carrier in a second step with a solution of sodium nitroferricyanide in a solvent mixture one component of which is methanol and drying again.

The urine of persons suffering from diabetes mellitus contains ketone bodies due to fat metabolsm. The detection of said ketone bodies (acetoacetic acid and acetone) in urine is, therefore, very important to the diagnosis of diabetes and to the stabilization and control of diabetics. The Legal test initially used for this purpose, i.e., the reaction of ketone bodies with sodium nitroferricyanide in an alkaline medium with formation of red to violet compounds, which can only be carried out with freshly prepared solutions because of the decomposition of sodium nitroferricyanide in alkaline solution, was later on replaced by a tablet containing all reagents, which is, of course, more easy to handle.

There have also been produced test strips, which are still more convenient to handle, containing all reagents necessary for the reaction on an absorbent carrier (cf. U.S. Pat. No. 3,212,855). To improve the storability of the sodium nitroferricyanide on the strips a film-forming organic substance must protect it from the basic buffer. This protection reduces however the reaction speed, so that the test strips have only limited utility.

British Specification No. 1,369,138 describes another process for preparing test strips, wherein paper is impregnated in a first step with the tetrasodium salt of ethylenediamino-tetraacetic acid and an amino acid, for example glycine. After drying the basically buffered paper is impregnated with a solution of sodium nitroferricyanide in methanol and dimethyl formamide (DMF) and also dried. Because of the use of DMF no film-forming substance need be added. According to the aforesaid specification it is, however, only DMF which exhibits said effect.

DMF is, however, a relatively high boiling substance and as such it is difficult to remove from the carrier. Tests have revealed that even when the strips are dried for a prolonged period of time at 80° C DMF remains behind on the carrier material where it probably exerts the stabilizing effect. Owing to the fact that the amount of DMF remaining on the test paper after drying strongly depends on the conditions of production, the production of a paper having a constant reactivity can involve considerable difficulties. Moreover, DMF has to be considered an unhealthy substance.

It is therefore the object of the present invention to provide a test paper for the detection of ketone bodies in liquids without the use of DMF. Knowing the content of British Specification No. 1,369,138 it could not be expected that in the production of test strips for the detection of ketones DMF could be replaced by other solvents miscible with methanol and that nevertheless test papers having excellent properties could be obtained without using an organic film-forming material.

The present invention provides in a process for the production of a diagnostic agent for the detection of ketones, consisting of an absorbent carrier impregnated with sodium nitroferricyanide, an alkaline buffer substance and a water-soluble lower amino acid by impregnating the carrier in the first stage with an aqueous solution of the amino acid and tetrasodium ethylenediamine tetraacetate as buffer, drying the carrier, impregnating it in a second stage with a solution of sodium nitroferricyanide in a solvent mixture containing methanol as one component, and drying the carrier again, the improvement which comprises using a solvent mixture consisting of methanol and an organic solvent miscible with methanol which is not dimethyl formamide.

The chemical composition of the solvent to be used in the solvent mixture besides methanol is immaterial. Especially good results can be obtained with linear or branched aliphatic alcohols with 2 to 6 C-atoms and certain aprotic solvents such as tetramethyl urea and dimethyl acetamide. Gasoline and benzene are also suitable.

Hence, the process of the invention makes it possible to vary and to optimize the manufacturing process in such different areas as deleteriousness to health, combustibility, price, solubility and the like.

The proportion of the solvent used in addtion to methanol can vary within wide limits, it is only limited by the solubility of sodium nitroferricyanide in the solvent mixture and its miscibility with methanol.

The strips having especially good properties are obtained when the components of the solvent mixture are used in an amount such that the limit of solubility of sodium nitroferricyanide is reached.

The choice of the carrier material is also of minor importance. With regard to the processing conditions stable and non breaking papers will be used. Polyamide or polyester fleeces are also suitable. The sensitivity of the test strips can also be adapted to some extend to the intended use by the selection of the paper thickness.

The following examples illustrate the invention.

EXAMPLE 1

Paper Schleicher & Schüll No. 2316 was impregnated with a solution 1 consisting of
  35 g of tetrasodium ethylenediamine tetraacetate
  12 g of glycine and
  0.2 g of optical brightener in
  76 ml of distilled water
and dried for 1 hour at 80° C. Subsequently the treated paper was impregnated with a solution 2 consisting of
  2 g of sodium nitroferricyanide in
  70 ml of methanol and
  30 ml of 2-methyl-butan-2-ol
and dried for 15 minutes at 80° C.

To prepare solution 2 the sodium nitroferricyanide was first dissolved in methanol and the 2-methyl-butan-2-ol was then added.

The paper treated in this manner indicated a content of 5 to 10 mg of acetoacetic acid/100 ml of solution and a content of 20 to 50 mg of acetone/100 ml of solution.

Equally valuable papers were obtained when 2-methyl-butan-2-ol was replaced by the same amount of
  n-butanol or
  tert.-butanol, or
  isopropanol, or
  amyl alcohol, or ethyl glycol (glycol monoethyl ether).

EXAMPLE 2

Paper Schleicher & Schüll No. 2316 was treated, as described in Example 1, with solution 1. The treated paper was then impregnated with one of the following impregnating solutions each containing 2 g of sodium nitroferricyanide in 100 ml of the specified solvent mixture and dried for 15 minutes at 80° C.

a. 30 ml of methanol and 70 ml of propanol
b. 40 ml of methanol and 60 ml of propanol
c. 50 ml of methanol and 50 ml of propanol
d. 60 ml of methanol and 40 ml of propanol.

As regards their sensitivity the test papers prepared in this manner were equivalent to the papers described in Example 1. After having been stored for 12 hours in normal laboratory atmosphere their stability was at least equal to that of the papers prepared according to British Specification No. 1,369,138 with dimethyl formamide as second component of the solvent mixture.

EXAMPLE 3

Without alteration of the sensitivity of the test paper the propanol used in Example 2 could be replaced by n-butanol or tert.-butanol.

EXAMPLE 4

Paper Schleicher & Schüll No. 2316, impregnated with solution 1 of Example 1 was treated with the following solution 2 and dried for 1 hour at 80° C.
Solution 2:
2 g of sodium nitroferricyanide
70 ml of methanol
30 ml of N-methylpyrrolidone A paper of this type satisfactorily indicated 10 mg of acetoacetic acid and 30 mg of acetone per 100 ml of solution.

Test papers prepared with the use of tetramethyl urea or dimethyl acetamide instead of N-methylpyrrolidone had the same sensitivity.

EXAMPLE 5

Paper Schleicher & Schull No. 2316 was impregnated with solution 1 of Example 1 and thereafter with the following solution 2 and dried for 15 minutes at 80° C:
Solution 2:
2 g of sodium nitroferricyanide dissolved in
50 ml of methanol and admixed with
50 ml of dioxane The paper obtained indicated 100 mg of acetone/100 ml of solution and 20 mg of acetoacetic acid/100 mg of solution.

What is claimed is:

1. In a process for the production of a diagnostic agent for the detection of ketones, consisting of an absorbent carrier impregnated with sodium nitroferricyanide, an alkaline buffer substance and a water-soluble lower amino acid by impregnating the carrier in the first stage with an aqueous solution of the amino acid and tetrasodium ethylenediamine tetraacetate as buffer, drying the carrier, impregnating it in a second stage with a solution of sodium nitroferricyanide in a solvent mixture containing methanol as one component, and drying the carrier again, the improvement which comprises using a solvent mixture consisting of methanol and an organic solvent miscible with methanol which is not dimethyl formamide.

2. The process of claim 1, wherein the solvent miscible with methanol is a linear or branched aliphatic alcohol with 2 to 6 C-atoms.

3. The process of claim 2, wherein the alcohol is propanol.

4. The process of claim 3, wherein the solvent mixture contains from 10 to 90 parts by volume of methanol and from 90 to 10 parts by volume of propanol.

5. The process of claim 4, wherein the solvent mixture contains 50 parts by volume of methanol and 50 parts by volume of propanol.

6. In a process for the production of a diagnostic agent for the detection of ketones, consisting of an absorbent carrier impregnated with sodium nitroferricyanide, an alkaline buffer substance and a water-soluble lower amino acid by impregnating the carrier in the first stage with an aqueous solution of the amino acid and tetrasodium ethylenediamine tetraacetate as buffer, drying the carrier, impregnating it in a second stage with a solution of sodium nitroferricyanide in a solvent mixture containing methanol as one component, and again drying the carrier, the improvement which comprises using a solvent mixture consisting of 10 to 90 parts by volume of methanol and 90 to 10 parts by volume of a linear or branched aliphatic alcohol having 2 to 6 carbon atoms.

* * * * *